US005776758A

United States Patent [19]

Hamajima et al.

[11] Patent Number: 5,776,758
[45] Date of Patent: Jul. 7, 1998

[54] CYSTEINE PROTEASE DERIVED FROM PARASITIC HELMINTHS

[76] Inventors: Fusanori Hamajima, 2-1-704, Hikarigaoka 5-Chome, Nerima-ku, Tokyo; Mikio Yamamoto, 2-4-503, Namiki 3-Chome, Tokorozawa-shi, Saitama-ken; Sumiaki Tsuru, 9-7-303, Tagara 3-Chome, Nerima-ku, Tokyo; Kazuo Yamagami, 16-309, Hirosawa 1-Chome, Wako-shi, Saitama-ken, all of Japan

[21] Appl. No.: 451,409

[22] Filed: May 26, 1995

Related U.S. Application Data

[63] Continuation of Ser. No. 246,917, May 20, 1994, abandoned, which is a continuation of Ser. No. 920,092, Jun. 24, 1992, abandoned.

[30] Foreign Application Priority Data

Jul. 25, 1991 [JP] Japan ................................. 3-208546
Feb. 12, 1992 [JP] Japan ................................. 4-057189

[51] Int. Cl.$^6$ .................................................. C12N 9/50
[52] U.S. Cl. ................................................ 435/219; 435/212
[58] Field of Search ............................... 424/94.63, 94.65; 435/219; 514/2, 12

[56] References Cited

FOREIGN PATENT DOCUMENTS

| 0 059 346 A3 | 9/1982 | European Pat. Off. . |
| 0 100 366 | 2/1984 | European Pat. Off. . |
| 0 421 022 A1 | 4/1991 | European Pat. Off. . |

OTHER PUBLICATIONS

Clagett, J., et al., "Chymopapain C, an Immunosyppressive Protease", Chemical Abstracts, Abstract No. 142250g, 80:25 (Jun. 24, 1974).

Clagett, J., et al., "Chymopapain C, Immunosuppressive Protease", Chemical Abstracts, Abstract No. 144278w, 80:25 (Jun. 24, 1974).

Dowd, A., et al., "Purification and Characterisation of a Cysteine Proteinase Secreted by *Fasciola Hepatica*", Biochemical Society Transactions 20:1:86S (Feb., 1992).

Eakin, A., et al., "Amplification and Sequencing of Genomic DNA Fragments Encoding Cysteine Proteases From Parasites", Molecular and Biochemical Parasitology, 39:1–8 (1990).

Heffernan, M., et al., "Characterization of a Cathapsin–3 Proteinase Released by *Fasciola Hepatica* (Liver Fluke)", 19:1:27S (Feb., 1991).

Kierszenbaum, F., et al., "Trypanosomal Inmunosuppressive Factor: A Secretion Product(s) of *Trypanosoma cruzi* That Inhibits Proliferation and IL–2 Receptor Expression by Activated Human Peripheral Blood Mononuclear Cells", Journal of Immunology, 144:10:4000–4004 (May 15, 1990).

Accession No. S12099, Pamer et al. (1993) Cysteine Proteinase precursor, EMBL database, 1993.

Accession No. S07051, Mottram et al. (1990) Cysteine Proteinase, EMBL database, 1990.

Yamakami, K. et al. *Comp. Biochem. Physiol.* 87B(3):643–648 (1987) (abstract).

Song, C. et al. *Comp. Biochem. Physiol.* 95B(3):473–476 (1990).

Yamakami, K. et al. *Comp. Biochem. Physiol.* 95B(4):755–758 (1990).

*Primary Examiner*—Vasu S. Jagannathan
*Assistant Examiner*—Enrique Longton
*Attorney, Agent, or Firm*—Limbach & Limbach L.L.P.

[57] ABSTRACT

The immunosuppressive drug of the present invention can suppress both delayed-type hypersensitivity and antibody production against specific antigens and graft tissues and induce immunological tolerance to them by several administrations, instead of long continuous administration.

Cysteine protease, a secretory protein accumulated in the tissue of parasitic helminths, is extracted and purified. The cysteine protease is administered to a mammal and then tissue is implanted to the mammal. The immune response of the mammal against the tissue implant is suppressed even one year later.

13 Claims, 6 Drawing Sheets

|   | Identity % |
|---|---|
| a. | K K |  |
| b. | N | [44.0% / 200 amino acids] |
| c. | N | [43.5% / 200 amino acids] |
| d. | G F A | [43.2% / 213 amino acids] |
| e. | L V | [43.0% / 221 amino acids] |
| f. | L V | [39.9% / 208 amino acids] |

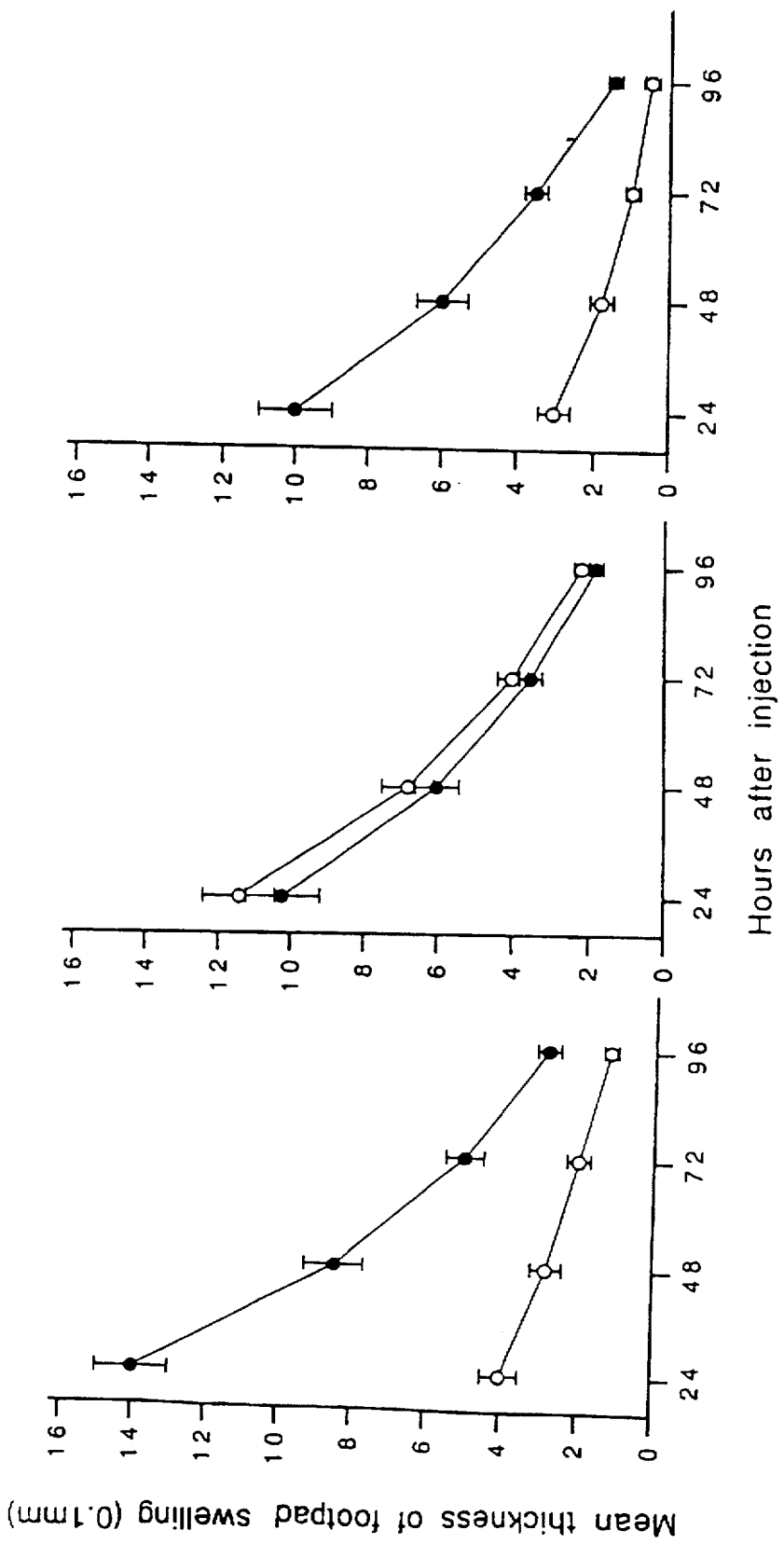

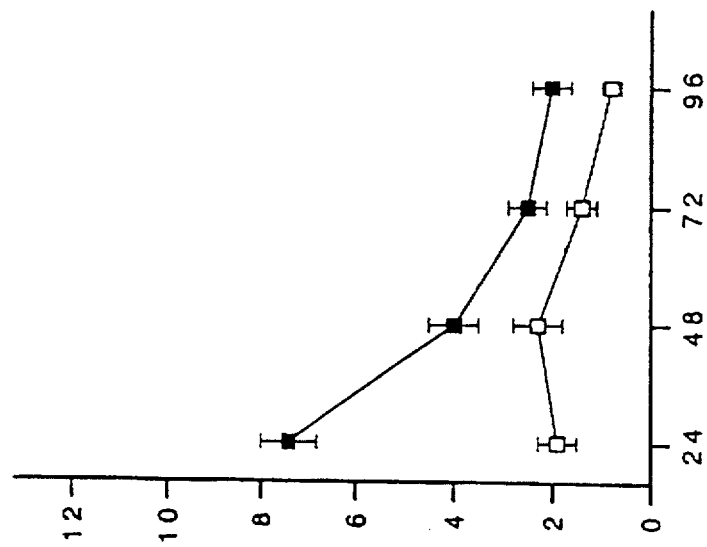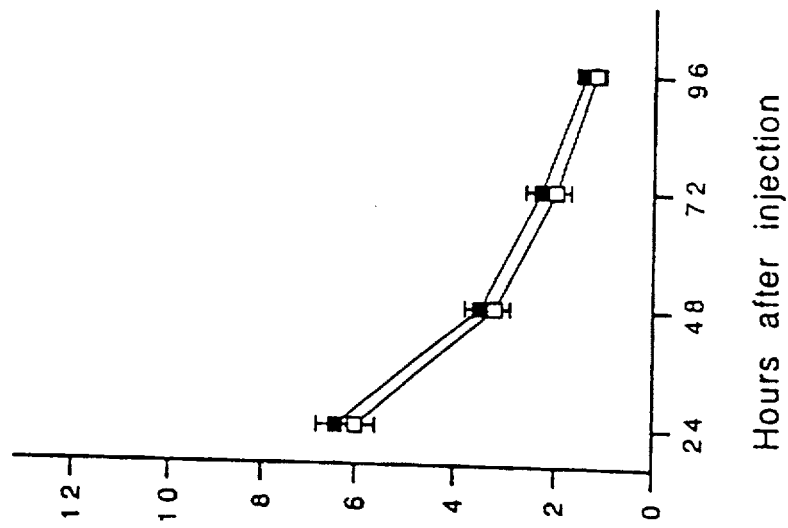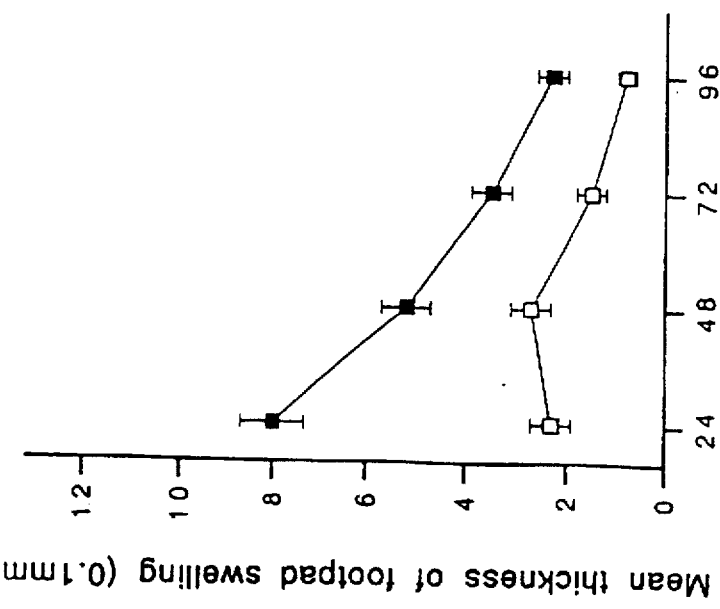

CYSTEINE PROTEASE DERIVED FROM PARASITIC HELMINTHS

This is a continuation of application Ser. No. 08/246,917 filed on May 20, 1994 which is a File Wrapper Continuation application of Ser. No. 07/920,092 filed on Jun. 24, 1992, both now abandoned.

FIELD OF THE INVENTION

The present invention relates to immunosuppressive drugs used for suppression of graft rejection in organ transplantation or suppression of autoimmune diseases.

BACKGROUND OF THE INVENTION

Currently, azathiopline, cyclosporin A, FK-506, and 15-deoxysperguarine are known as immunosuppressive drugs used for a therapeutic purpose, and have potent suppression effect.

However, the conventional immunosuppressive drugs do not induce immunological tolerance and are therefore required that the drug be continuously administered for a long period of time. Side effects such as cancer, nephrotoxicity, angiitis, hepatotoxicity and disorders in the digestive tract have resulted from the continuous administration of these doses.

The present inventors have studied agents of human parasites, especially parasitic helminths, which protect them from the immune response of human hosts, and have found that a cysteine protease, a secretory protein accumulated in the tissue of parasitic helminths, suppresses the cell-mediated and humoral immunities of mammalian hosts and induces the hosts to acquire immunological tolerance to the parasite.

SUMMARY OF THE INVENTION

The immunosuppressive drug of the present invention can suppress both delayed-type hypersensitivity and antibody production against specific antigens and graft tissues, and induce immunological tolerance by several administrations. Conventional immunosuppressive drugs are required that they be administered for a long period of time, and cause an adverse effect which is a drawback of the drugs. In contrast, it is not required that the immunosuppressive drug of the present invention it be administered for a long period of time. Therefore, the immunosuppressive drug of the invention overcomes the drawback of conventional immunosuppressive drugs.

DESCRIPTION OF THE FIGURES

Figure 1A:
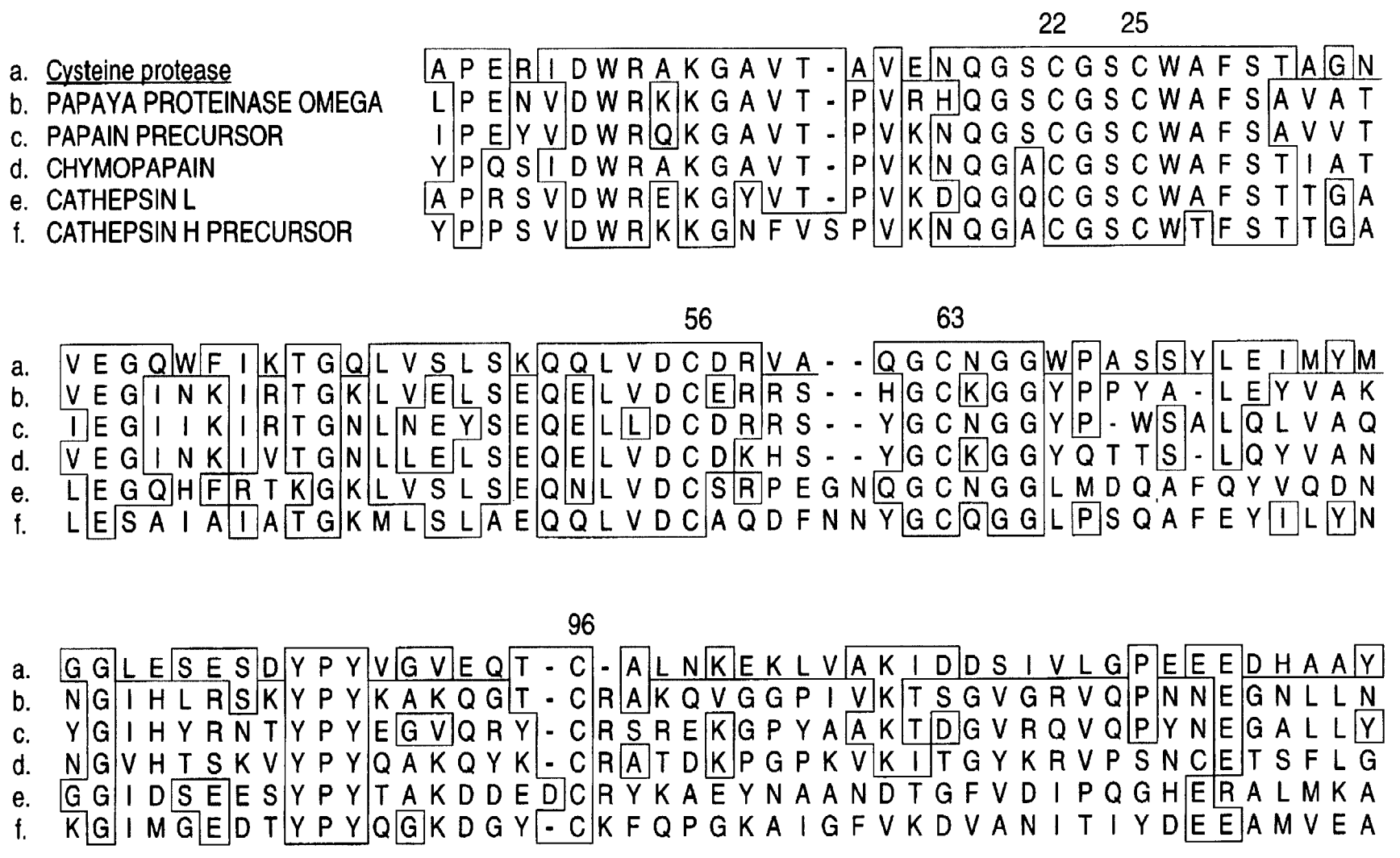
Figure 1B:
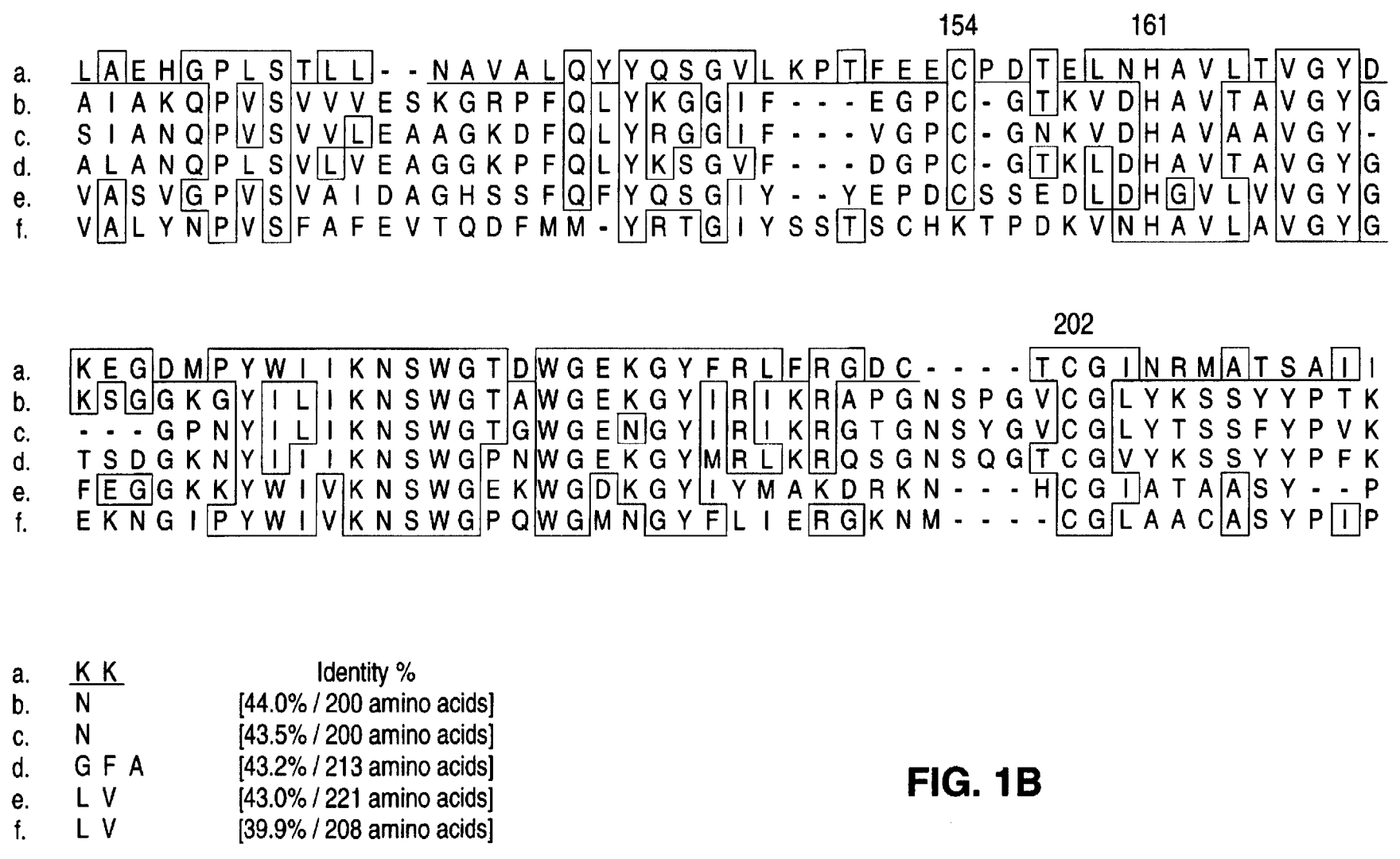

FIGS. 1A and 1B show a comparison of the deduced amino acid sequences of a cysteine protease from *Paragonimus westermani* metacercariae and other similar cysteine proteases. Homologous areas are boxed and heterologous amino acids are underlined.

FIGS. 3A, 3B and 3C are graphs showing a footpad response of $C_{57}BL/6$ female mice to sheep red blood cells (SRBC) and adult *Paragonimus westermani* antigens. The mice were immunized with SRBC one day after an injection of the present cysteine protease. Group treated with the protease on day-1 (○) and control group (●). Bars represent standard errors. (a) The initial SRBC injection one day after the protease treatment. (b) Adult *P. westermani* antigen injection six months after the initial SRBC immunization. (c) SRBC injection one year after the initial SRBC immunization.

FIGS. 4A, 4B and 4C are graphs showing a footpad response of $C_{57}BL/6$ male mice to adult *Paragonimus westermani* antigens and sheep red blood cells (SRBC). The mice were immunized with adult *Paragonimus westermani* antigens one day after injection of the present cysteine protease. Group treated with the protease on day-1 (□) and control group (●). Bars represent standard errors. (a) The initial adult *P. wetermani* antigen injection one day after the protease treatment. (b) SRBC injection six months after the initial adult *P. westermani* antigen immunization. (c) adult *P. westermani* antigen injection one year after the initial adult *P. westermani* antigen immunization.

DETAILED DESCRIPTION OF THE INVENTION

Figure 2:
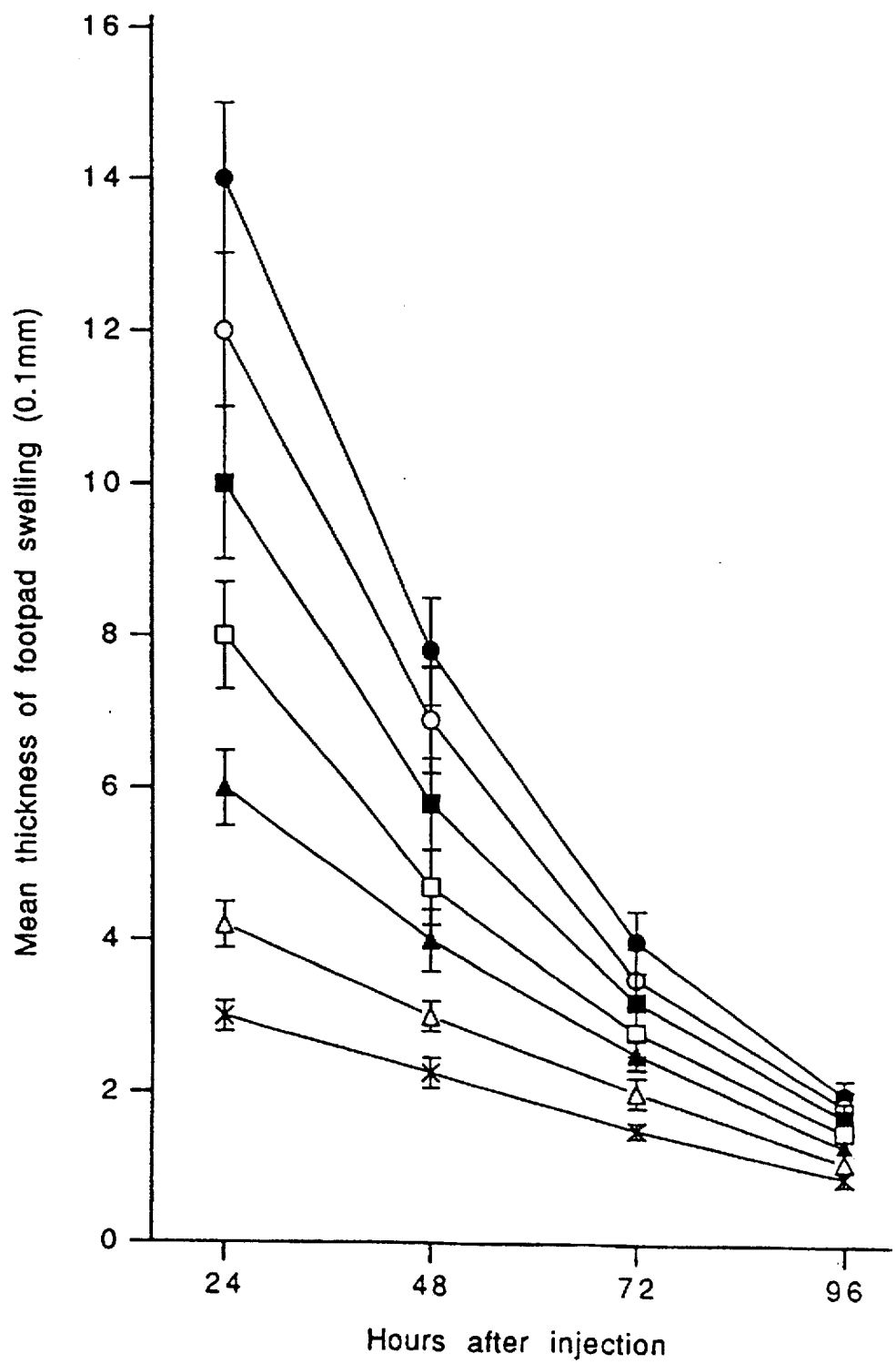
FIG. 2 is a graph showing a footpad response (swelling of footpad) of $C_{57}BL/6$ female mice. The female mice were intraperitoneally injected with sheep red blood cells (SRBC) at various times after intraperitoneal injection of the present cysteine protease. The intervals were 0(X), 1(△), 2(▲), 3 and 4(□), 5 and 6(■), 7 and 8 days (○) and untreated control (●). Bars represent standard errors.

It is an object of the present invention to provide immunosuppressive drugs which, without long continuous administration, suppress both delayed-type hypersensitivity and antibody production against specific antigens and graft tissues and induce immunological tolerance to specific antigens and grafted tissues.

The present invention is characterized by the following description.

(1). The present invention provides an immunosuppressive drug in which cysteine protease comprises its composition.

(2). The present invention provides the immunosuppressive drug of (1) in which the cysteine protease contains a larger amount of acidic amino acids than basic amino acids.

(3). The present invention provides the immunosuppressive drug of (1) or (2) in which the cysteine protease is active in neutral hydrogen ion concentration.

(4). The present invention provides the immunosuppressive drug of (1), (2), or (3) in which the cysteine protease is extracted from the infected larvae of parasitic helminths.

(5). The present invention provides the immunosuppressive drug of (1), (2), (3), or (4) in which the cysteine protease comprises an amino acid sequence described in SEQ ID No. 1.

(6). The present invention provides a cysteine protease having an amino acid sequence described in SEQ ID No. 1.

(7). The present invention provides a cysteine protease gene encoding a polypeptide having an amino acid sequence described in SEQ ID No. 1.

(8). The present invention provides a cysteine protease gene having a base sequence described in SEQ ID No. 2.

The term, "cysteine protease" of the present invention is intended to mean an endopeptidase comprising cysteine residues at amino acid positions, 22, 25, 56, 63, 96, 154, and 202, and a histidine residue at amino acid position 161 (the position is numbered from N terminus in the amino acid sequence) and having an active center at cysteine and histidine residues.

The immunosuppressive drug of the invention comprises cysteine protease directly obtained by extracting the cell and tissue of organisms including invertebrates such as parasitic helminths to vertebrates such as various animals including mammal, or by cultured cells isolated from organisms described above, or by genetic engineering using recombinant DNA containing a cysteine protease gene (recombinant DNA technique), or by chemical synthesis.

When the cysteine protease of the present invention (hereinafter referred to as "present cysteine protease") is injected within a few days and/or several days before an injection of an antigen, the injection of the present cysteine protease suppresses cell-mediated immune response and/or humoral immune response, which is antibody production, against the antigen, for a long period of time. In addition, such a prior injection of the present cysteine protease allow hosts to take a graft for a long period of time and induce the hosts to acquire immunological tolerance to the graft.

Although the detailed mechanism of how cysteine protease works on the immune system is not clearly understood, it is believed that the immunosuppressive drug of the invention administered to a mammalian host is involved with the antigen presentation of immunocytes, receptors or suppressor T cells, thereby suppressing both delayed-type hypersensitivity and antibody production and inducing the immunological tolerance of the mammalian host.

The present invention will be further described in Examples, which are not intended to limit the scope of the invention.

EXAMPLE

1. Extraction and Purification of Cysteine Protease from Parasitic Helminth

The cysteine protease of the invention was obtained by extracting *Paragonimus westermani* metacercaria with 50 mM imidazole-HCl/pH7.0, subjecting the extract to centrifugation (at 105,000 g, for 60 minutes), loading the supernatant onto Arginine-Sepharose CL-4B affinity chromatography, filtering the eluate on an Ultrogel AcA-54 gel and purifying the filtrate by DEAE-toyopearl S column chromatography. N-terminal 25 amino acids of the purified native cysteine protease is shown in SEQ ID No. 5.

2. Amino Acid and Base Sequence of Present Cysteine Protease

The purified present cysteine protease was emulsified with Freund's complete adjuvant. The emulsion was intravenously injected in the ears of rabbits for immunization, and antiserum against the present cysteine protease was obtained.

About $2\times10^4$ *Paragonimus westermani* metacercariae were used to obtain mRNA. Total RNA (about 100 μg) was extracted from the pooled material by phenol extraction and poly $A^+$RNA (about 2 μg) was recovered by passing the total RNA through an oligo (dT)-cellulose column. The mRNA thus obtained was used to construct a cDNA library using the λgt11 vector. The cDNA library was screened by the antiserum and 25 independent positive clones containing about 300–600 bp long insert were obtained. Of 25 clones, two clones having the longest cDNA sequence were designated as λPW6 and λPW24. The two clones were subcloned using pUC118, and the two subclones were named pPW6 and pPW24, respectively. Then, the base sequences of the two clones were determined by the dideoxy nucleotide sequencing method using a T7 sequencing kit (United States Biochemicals, U.S.A.).

*E. coli* MV1184 was transformed with the subclone pPW6 and the transformant, *E. coli* MV1184/pPW6, was deposited with Fermentation Research Institute, Agency of Industrial Science and Technology and was assigned the accession number FERM BP-3937.

The base sequence and deduced amino acid sequence of pPW6 and pPW24 are shown in SEQ ID Nos. 3 and 4, respectively. Primers were synthesized based on the sequence near the ends of the cDNA insert of the clone and were used to screen the cDNA library again by the PCR.

A base sequence including the entire coding region of the gene of one mature cysteine protease of *Paragonimus westermani* metacercaria was determined (SEQ ID No. 2). The mRNA sequence contains an open reading frame with a significant length. The deduced amino acid sequence is shown in SEQ ID No. 1. The base sequence of the other several cDNA clones strongly suggested that each protease has a few different amino acids and belongs to a closely related protein family. The mature cysteine protease of the invention was found to contain 215 amino acids.

3. Characterization of Amino Acid Sequence of Present Cysteine Protease

The comparison of the primary structures of the present cysteine protease and the cysteine protease of other species (hereinafter referred to as "similar cysteine proteases") has revealed the following features: an amino acid sequence (boxed region) in FIG. 1 is homologous in both the present cysteine protease and similar cysteine proteases; cysteine residues are found at amino acid positions, 22, 25, 56, 63, 96, 154, and 202, and a histidine residue is found at amino acid position 161, the position that is numbered from N terminus in the amino acid sequence. This primary structure suggests that the present cysteine protease has a typical feature of cysteine protease. However, the underlined amino acid sequence of the present cysteine protease is different from those of all the other similar cysteine proteases.

In addition, the base sequences of other clones have revealed some substitutions of amino acid residues: in the present cysteine protease, there are substitutions, Ala→Pro (amino acid position 15), Ser→Glu (21), Argo→Met (58), Val→Ala (59), Gln→Glu (61), Ala→Ser (69), and Tyr→Asp (77), the position that is numbered from N terminus in the amino acid sequence. This amino acid substitution strongly suggests that the primary structure of the present cysteine protease is at least 90% homologous to the other cysteine protease and that the present cysteine protease has a few different amino acids from other cysteine proteases to form its own family. These findings also coincide with variability found in the serine proteases of nematodes and are believed to be the common feature of parasitic helminths.

Furthermore, there is a difference in the number of amino acid residues between cysteine at amino acid position 56 and the following cysteine: 6 amino acid residues are found in the present cysteine protease, papain, chymopapain and papaya proteinase while 8 amino acid residues are found in cathepsin L and H. Based on the known three-dementional structure of papain, it is believed that the present cysteine protease forms a disulfide bridge at amino acid positions 22–63, 56–96 and 154–202, and its active site residue is cysteine at amino acid position 25 and histidine at 161.

The present cysteine protease is composed of more acidic amino acids(14.89–14.96 mole % acidic amino acid such as glutamic acid and aspartic acid) than basic amino acid (10.17–10.23 mole % basic amino acid such as lysine and arginine). The amino acid composition is similar to that of cathepsin L, but different from those of papain, chymopapain and papaya proteinase, which contains more basic amino acids (13.66–14.29 mole %) than acidic amino acids (7.08–8.37 mole %) (see Table 1). In order that a cysteine protease works well in the neutral or faint acidic environment of the organism, it appears reasonable that the cysteine protease have a high acidic amino acid content. The high acidic amino acid content of the present cysteine protease is believed to be the reason that the present cysteine protease alone has an immunosuppressive effect while other similar cysteine proteases such as papain and the like do not.

The present cysteine protease contains leucine in a large amount (8.10–8.14 mole %) and asparagine and tyrosine in a small amount –3.86 and 5.95–6.58 mole %, respectively), a prominent feature that distinguishes the present cysteine protease from other similar cysteine proteases (Table 1).

TABLE 1

Amino acid composition of a cysteine protease and other homologous cysteine proteases

| Amino acid | Mol % | | | | | |
|---|---|---|---|---|---|---|
| | CP* | PPA* | CPPA* | PP* | CL* | CH* |
| Glutamic acid | 9.09 | 5.93 | 3.73 | 5.44 | 9.30 | 5.23 |
| Leucine | 8.10 | 5.29 | 5.71 | 4.85 | 5.17 | 5.13 |
| Valine | 5.96 | 7.72 | 6.80 | 9.09 | 6.63 | 6.25 |
| Glycine | 6.00 | 7.70 | 7.35 | 8.04 | 6.63 | 6.14 |
| Aspartic acid | 5.80 | 2.44 | 3.35 | 2.46 | 6.12 | 4.26 |
| Alanine | 5.83 | 4.57 | 4.52 | 4.61 | 5.04 | 6.02 |
| Lysine | 6.37 | 5.36 | 11.13 | 7.56 | 6.72 | 7.27 |
| Glutamine | 5.31 | 5.35 | 5.83 | 6.48 | 4.13 | 5.19 |
| Threonine | 4.76 | 3.05 | 6.05 | 3.96 | 3.37 | 4.23 |
| Tryptophan | 5.19 | 3.74 | 2.96 | 3.02 | 3.61 | 3.63 |
| Asparagine | 3.36 | 5.81 | 5.27 | 6.83 | 5.14 | 5.64 |
| Serine | 5.35 | 5.01 | 6.48 | 6.99 | 7.06 | 4.86 |
| Cysteine | 3.52 | 3.11 | 3.51 | 2.69 | 3.00 | 3.45 |
| Methionine | 2.17 | 0.00 | 0.54 | 0.00 | 3.16 | 3.71 |
| Tyrosine | 6.58 | 12.61 | 9.86 | 8.70 | 8.33 | 9.65 |
| Arginine | 3.80 | 8.30 | 3.16 | 6.44 | 3.69 | 1.86 |
| Proline | 3.35 | 4.22 | 4.59 | 3.40 | 3.66 | 4.91 |
| Phenylalanine | 3.00 | 2.42 | 3.59 | 1.83 | 4.67 | 5.87 |
| Isoleucine | 4.77 | 6.25 | 3.80 | 5.33 | 2.78 | 5.60 |
| Histidine | 1.69 | 1.14 | 1.68 | 2.29 | 1.64 | 1.10 |

*CP: Cysteine protease, PPA: Papain, CPPA: Chymopapain, PP: Papaya proteinase, CL: Cathepsin L, CH: Cathepsin H 4 Suppressive Effects of Present Cysteine Protease on Cell-mediated Immune Response and Humoral Immune Response.

12-week old C57BL/6 female mice were divided into 10 groups, each group having 6 mice. The present cysteine protease was intraperitoneally administered (100 ng protein per mouse which is an enough concentration to suppress footpad reaction) to the mice, except for a control group, 1, 2, 3, 4, 5, 7, and 8 days before the administration of antigens and on the same day when antigens were administered. The mice were immunized with the intraperitoneal injection of $1 \times 10^8$ sheep red blood cells (SRBC) suspended in 0.1 ml of phosphate buffed saline (PBS) as an initial antigen. Five days later, $5 \times 10^7$ SRBCs suspended in 0.05 ml PBS as booster was injected to the footpad. Then, degree of swelling (thickness) was measured (Experimental schedule 1 shown in Table 2).

TABLE 2

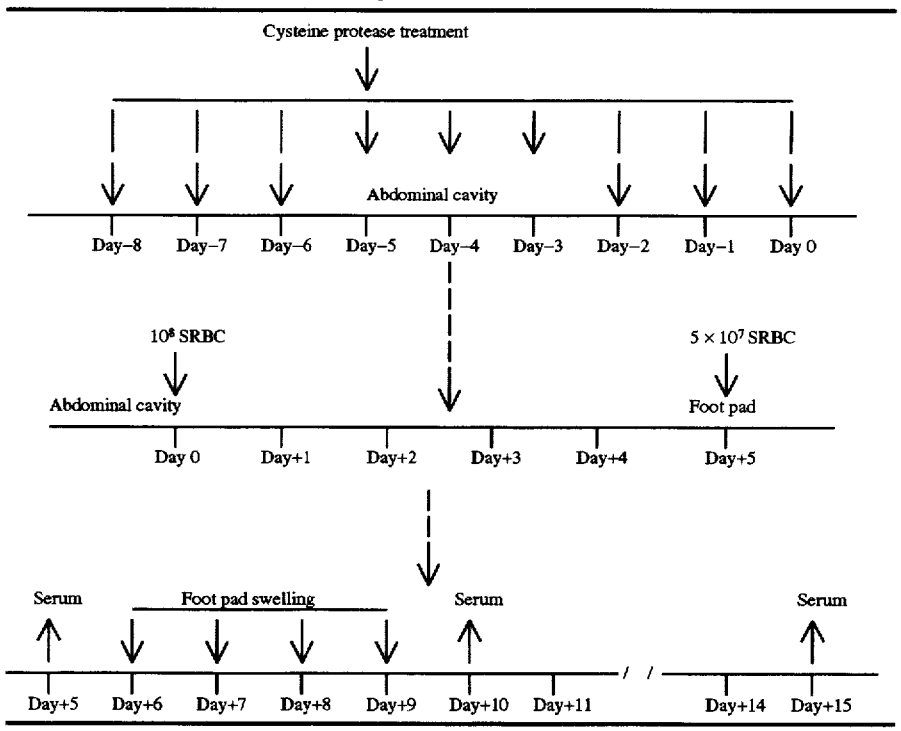

Compared with control, footpad reaction (swelling) was significantly suppressed in the group (P<0.01) to which present cysteine protease was administered one day before immunization. This result suggests that administration of the present cysteine prolease suppresses delayed-type hypersensitivity, against SRBC (FIG. 2).

Each group of mice was tested for the antibody titer (HA) of blood serum using SRBC. Compared with control, antibody production was significantly suppressed in the group of mice to which the present cysteine protease was administered 4–5 days before the injection of the antigen (Table 3).

TABLE 3

Antibody production in serum of $C_{57}BL/6$ female mice injected intraperitoneally with SRBC immunization at various days after treatment of cysteine protease

| Day of CP treatment | Anti-SRBC (HA) titer ($Log_2$) on 15 days after immunization Mean ± SE |
|---|---|
| Day 0 | 6.0 ± 0.26 |
| Day-1 | 5.5 ± 0.22 |
| Day-2 | 5.0 ± 0.31 |
| Day-3 | 4.2 ± 0.31 |
| Day-4 | 3.0 ± 0.31 |
| Day-5 | 2.2 ± 0.17 |
| Day-6 | 3.3 ± 0.37 |
| Day-7 | 4.5 ± 0.22 |
| Day-8 | 5.0 ± 0.30 |
| Control | 5.5 ± 0.34 |

CP (Cysteine protease) and SE (Standard error)

5 Immunological Tolerance Induced by Present Cysteine Protease

The present protease (100 ng protein per mouse) was intraperitoneally administered to 12-week old B57BL/6 female and male mice. One day later, a group was immunized with SRBC or adult *Paragonimus westermani* antigens (Experimental schedule 2 shown in Table 4). The group demonstrated the suppression of a footpad reaction against SRBC or adult *Paragonimus westermani* antigens even one year after the initial immunization (FIGS. 3 and 4). In these groups, the immunosuppression was specifically occurred to the antigen that was initially injected before one year while no immunosuppression of a footpad reaction was occurred to other antigens (FIGS. 3 and 4).

TABLE A

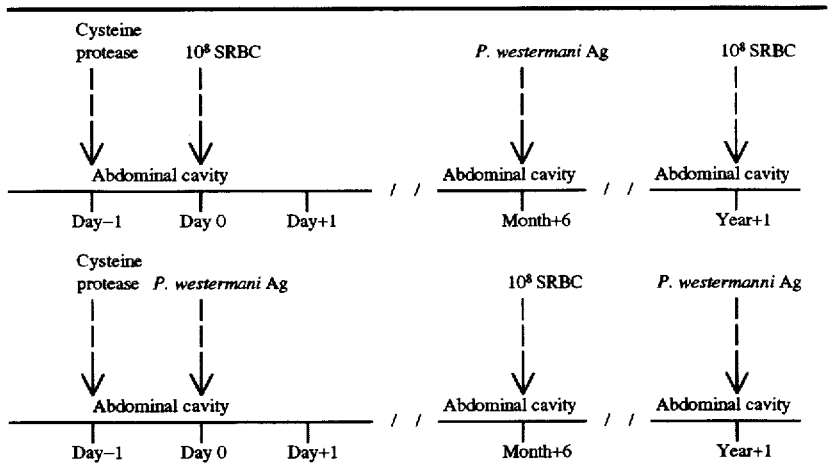

As is shown in Experimental schedule 3 in Table 5, when the skin of 8-week old, AKR female mice was implanted to 10-week old, C3H/He female mice to which the present cysteine protease (total amount, 1.5 μg protein) had been administered one and 4 days before implantation, the administered group took the graft for a significantly longer period of time (P<0.05–0.01; mean survival time: 100±36) than control (mean survival time: 18±0.5 days) (Table 6).

TABLE 5

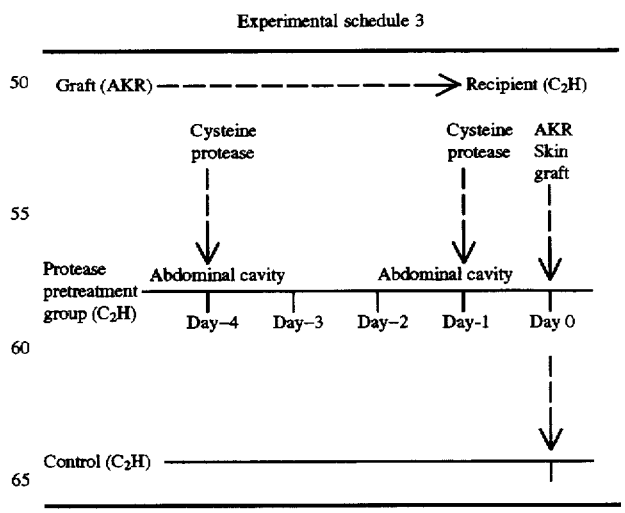

TABLE 6

Effects of CP treatment on the survival of skin allografts

| Recipient | Donor of skin grafts | CP dose schedule (μg/Kg) Day-4 | CP dose schedule (μg/Kg) Day-1 | Skin allograft survival time (days) in individual mice | MST(day) ± SE | P value (t-test) | No. of hair growth | P value ($x^2$-test) |
|---|---|---|---|---|---|---|---|---|
| C₃H/He ♀ | ARK ♀ | — | — | 17,17,18,18,19,20 | 18 ± 0.5 | <0.05 | 0 | <0.01 |
|  |  | 30 | 15 | 20 > 30 > 60 > 90 > 150 > 250 | 100 ± 36 |  | 5 |  |

The abbreviations are mean survival time (MST), standard error (SE) and cysteine protease (CP)

As is evident from the results, the present cysteine protease intraperitoneally administered to mice was found to induce immunological tolerance to the antigen or the tissue which were injected or implanted immediately after the administration of the present cysteine protease.

6. Immunological Tolerance of Other Protease Species

Figure 5:
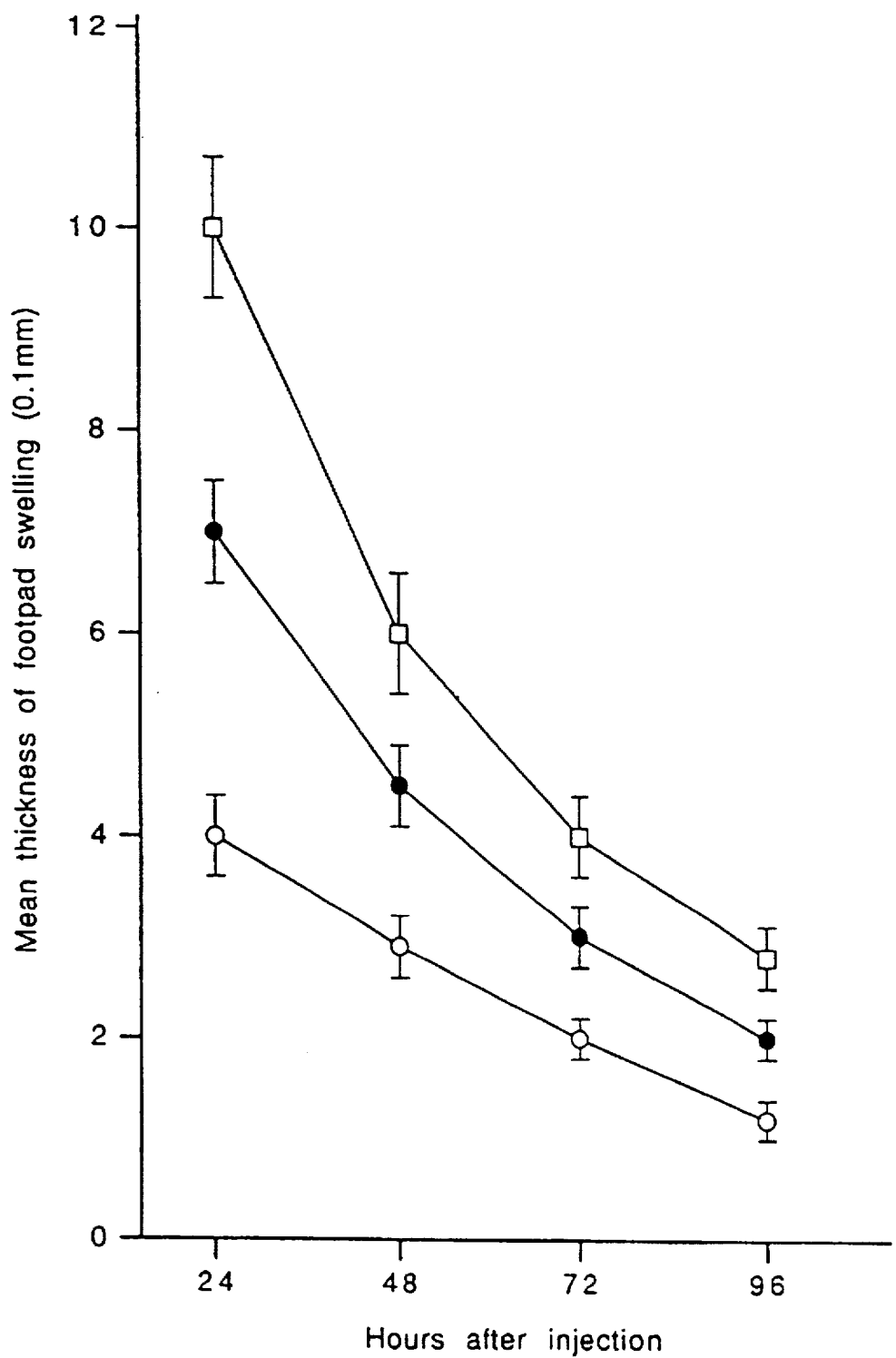
FIG. 5 is a graph showing a footpad response of $C_{57}BL$ female mice to sheep red blood cells (SRBC). The mice were immunized with SRBC one day after injection of various cysteine proteases. Groups treated with plasmin, trypsin, papain, cathepsin $B_1$ and untreated control (□),collagenase (●), and *P. westermani* cysteine protease (○). Bars represent standard errors.

Most of the different proteases (e.g., 100 ng of Plasmin, Trypsin, Cathepsin B1, Papain, or Collagenase per mouse) intraperitoneally administered to 12-week old, C57BL/6 female mice did not induce immunological tolerance (FIG. 5). Weak suppression of a footpad reaction was observed in the collagenase administered group but no immunosuppression was observed one year later.

As is evident from the above experiment, the administration of the present cysteine protease suppresses delayed-type hypersensitivity and antibody production against specific antigens and implants, and induces immunological tolerance in the mice.

Pharmaceutical agents utilizing the immunosuppressive effects of the present cysteine protease for therapeutic purpose may be in various forms including an injectable solution described in Example, inhalant, ointment, or a lyophilized form. Dosage may depend on how the present cysteine protease is administered and what therapeutic purpose one is in need.

Although the present cysteine protease used in Example is one that is directly extracted from parasitic helminths, an amount of the cysteine protease that is extracted from one parasitic helminth is a very small. For the isolation and purification of the cysteine protease, it not only takes long time but is also costly so that it is desirable for a commercial scale of the preparation of the cysteine protease to produce it in a large amount by cultured animal cells or by genetic engineering using recombinant DNA containing a gene of interest (recombinant DNA technology).

---

What is claimed is:

1. A composition comprising a biologically active cysteine protease derived from parasitic helminths wherein the amino acid sequence is at least 90% identical to the amino acid sequence of SEQ ID No. 1.

2. The composition of claim 1 wherein the cysteine protease has an amino acid sequence in which the total number of acidic amino acid residues in the sequence exceeds the total number of basic amino acid residues in the sequence.

3. The composition of claim 1 wherein the cysteine protease is active at about pH 7.

4. The composition of claim 2 wherein the cysteine protease is active at about pH 7.

5. The composition of claim 2 wherein the cysteine protease has the amino acid sequence of SEQ ID No. 1.

6. The composition of claim 3 wherein the cysteine protease has the amino acid sequence of SEQ ID No. 1.

7. The composition of claim 4 wherein the cysteine protease has the amino acid sequence of SEQ ID No. 1.

8. A composition comprising a biologically active cysteine protease derived from parasitic helminths wherein the amino acid sequence is at least 90% identical to the amino acid sequence of SEQ ID No. 1 and wherein the amino acid sequence of the cysteine protease has a proline residue at position 15, a glutamate residue at positions 21 and 61, a cysteine residue at positions 22, 25, 56, 63, 96, 154 and 202, a methionine residue at position 58, an alanine residue at position 59, a serine residue at position 69, an aspartate residue at position 77 and a histidine residue at position 161, wherein the amino acid residue positions are relative to the N terminus.

9. The composition of claim 8 wherein the cysteine protease has an amino acid sequence in which the total number of acidic amino acid residues in the sequence exceeds the total number of basic amino acid residues in the sequence.

10. The composition of claim 8 wherein the cysteine protease is active at about pH 7.

11. The composition of claim 8 wherein the cysteine protease is from infected larvae of parasitic helminths.

12. A composition comprising a cysteine protease with an amino acid sequence of SEQ ID number 1.

13. A composition comprising a biologically active cysteine protease derived from parasitic helminths wherein the amino acid sequence is at least 90% identical to the amino acid sequence of SEQ ID No. 1 and wherein the amino acid sequence of the cysteine protease has a proline residue at position 15, a glutamate residue at positions 21 and 61, a cysteine residue at positions 22, 25, 56, 63, 96, 154 and 202, a methionine residue at position 58, an alanine residue at position 59, a serine residue at position 69, an aspartate residue at position 77 and a histidine residue at position 161, wherein the amino acid residue positions are relative to the N terminus wherein the cyateine protease has an amino acid sequence in which the total number of acidic amino acid residues in the sequence exceeds the total number of basic amino acid residues in the sequence wherein the cysteine protease is active at about pH 7.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 215
        ( B ) TYPE:amino acid
        ( C ) STRANDEDNESS:
        ( D ) TOPOLOGY:Linear ( i i ) MOLECULE TYPE:peptide ( v i ) ORIGINAL SOURCE:
        ( A ) ORGANISM:Paragonimus westermani metacecaria
        ( B ) CELL TYPE:
        ( C ) CELL LINE:

( i x ) FEATURE:
        ( A ) LOCATION: 5
        ( B ) NAME/KEY: Xaa:Met or Ile ( i x ) FEATURE:
        ( A ) LOCATION:15
        ( B ) NAME/KEY:Xaa:Ala or Pro ( i x ) FEATURE:
        ( A ) LOCATION:21
        ( B ) NAME/KEY:Xaa:Ser or Glu ( i x ) FEATURE:
        ( A ) LOCATION:58
        ( B ) NAME/KEY:Xaa:Arg or Met ( i x ) FEATURE:

(A) LOCATION: 59
(B) NAME/KEY: Xaa: Val or Ala (ix) FEATURE:
  (A) LOCATION: 61
  (B) NAME/KEY: Xaa: Gln or Glu (ix) FEATURE:
  (A) LOCATION: 69
  (B) NAME/KEY: Xaa: Ala or Ser (ix) FEATURE:
  (A) LOCATION: 77
  (B) NAME/KEY: Xaa: Tyr or Asp (xi) SEQUENCE DESCRIPTION: SEQ ID NO:1:

| Ala | Pro | Glu | Arg | Xaa | Asp | Trp | Arg | Ala | Lys |
|---|---|---|---|---|---|---|---|---|---|
|   |   |   |   | 5 |   |   |   |   | 10 |
| Gly | Ala | Val | Thr | Xaa | Val | Glu | Asn | Gln | Gly |
|   |   |   |   | 15 |   |   |   |   | 20 |
| Xaa | Cys | Gly | Ser | Cys | Trp | Ala | Phe | Ser | Thr |
|   |   |   |   | 25 |   |   |   |   | 30 |
| Ala | Gly | Asn | Val | Glu | Gly | Gln | Trp | Phe | Ile |
|   |   |   |   | 35 |   |   |   |   | 40 |
| Lys | Thr | Gly | Gln | Leu | Val | Ser | Leu | Ser | Lys |
|   |   |   |   | 45 |   |   |   |   | 50 |
| Gln | Gln | Leu | Val | Asp | Cys | Asp | Xaa | Xaa | Ala |
|   |   |   |   | 55 |   |   |   |   | 60 |
| Xaa | Gly | Cys | Asn | Gly | Gly | Trp | Pro | Xaa | Ser |
|   |   |   |   | 65 |   |   |   |   | 70 |
| Ser | Tyr | Leu | Glu | Ile | Met | Xaa | Met | Gly | Gly |
|   |   |   |   | 75 |   |   |   |   | 80 |
| Leu | Glu | Ser | Glu | Ser | Asp | Tyr | Pro | Tyr | Val |
|   |   |   |   | 85 |   |   |   |   | 90 |
| Gly | Val | Glu | Gln | Thr | Cys | Ala | Leu | Asn | Lys |
|   |   |   |   | 95 |   |   |   |   | 100 |
| Glu | Lys | Leu | Val | Ala | Lys | Ile | Asp | Asp | Ser |
|   |   |   |   | 105 |   |   |   |   | 110 |
| Ile | Val | Leu | Gly | Pro | Glu | Glu | Glu | Asp | His |
|   |   |   |   | 115 |   |   |   |   | 120 |
| Ala | Ala | Tyr | Leu | Ala | Glu | His | Gly | Pro | Leu |
|   |   |   |   | 125 |   |   |   |   | 130 |
| Ser | Thr | Leu | Leu | Asn | Ala | Val | Ala | Leu | Gln |
|   |   |   |   | 135 |   |   |   |   | 140 |
| Tyr | Tyr | Gln | Ser | Gly | Val | Leu | Lys | Pro | Thr |
|   |   |   |   | 145 |   |   |   |   | 150 |
| Phe | Glu | Glu | Cys | Pro | Asp | Thr | Glu | Leu | Asn |
|   |   |   |   | 155 |   |   |   |   | 160 |
| His | Ala | Val | Leu | Thr | Val | Gly | Tyr | Asp | Lys |
|   |   |   |   | 165 |   |   |   |   | 170 |
| Glu | Gly | Asp | Met | Pro | Tyr | Trp | Ile | Ile | Lys |
|   |   |   |   | 175 |   |   |   |   | 180 |
| Asn | Ser | Trp | Gly | Thr | Asp | Trp | Gly | Glu | Lys |
|   |   |   |   | 185 |   |   |   |   | 190 |
| Gly | Tyr | Phe | Arg | Leu | Phe | Arg | Gly | Asp | Cys |
|   |   |   |   | 195 |   |   |   |   | 200 |
| Thr | Cys | Gly | Ile | Asn | Arg | Met | Ala | Thr | Ser |
|   |   |   |   | 205 |   |   |   |   | 210 |

Ala Ile Ile Lys Lys
            215

( 2 ) INFORMATION FOR SEQ ID NO:2:

( i ) SEQUENCE CHARACTERISTICS:
        ( A ) LENGTH: 648
        ( B ) TYPE:nucleic acid
        ( C ) STRANDEDNESS: single
        ( D ) TOPOLOGY: linear ( i i ) MOLECULE TYPE:cDNA to mRNA ( v i ) ORIGINAL SOURCE:
        ( A ) ORGANISM:Paragonimus westermani metacecaria
        ( B ) CELL TYPE:
        ( C ) CELL LINE:

( i x ) FEATURE:

( i x ) FEATURE:
        ( A ) LOCATION:15
        ( B ) NAME/KEY:N:T or G ( i x ) FEATURE:
        ( A ) LOCATION:43
        ( B ) NAME/KEY:N:G or C ( i x ) FEATURE:
        ( A ) LOCATION:48
        ( B ) NAME/KEY:N:T or G ( i x ) FEATURE:
        ( A ) LOCATION:61
        ( B ) NAME/KEY:N:T or G ( i x ) FEATURE:
        ( A ) LOCATION:62
        ( B ) NAME/KEY:N:C or A ( i x ) FEATURE:
        ( A ) LOCATION:66
        ( B ) NAME/KEY:N:C or T ( i x ) FEATURE:
        ( A ) LOCATION:123
        ( B ) NAME/KEY:N:A or G ( i x ) FEATURE:
        ( A ) LOCATION:173
        ( B ) NAME/KEY:N:G or T ( i x ) FEATURE:
        ( A ) LOCATION:176
        ( B ) NAME/KEY:N:T or C ( i x ) FEATURE:
        ( A ) LOCATION:181
        ( B ) NAME/KEY:N:C or G ( i x ) FEATURE:
        ( A ) LOCATION:205
        ( B ) NAME/KEY:N:G or T ( i x ) FEATURE:
        ( A ) LOCATION:213
        ( B ) NAME/KEY:N:C or A ( i x ) FEATURE:
        ( A ) LOCATION:229
        ( B ) NAME/KEY:N:T or G ( i x ) FEATURE:
        ( A ) LOCATION:237
        ( B ) NAME/KEY:N:C or T ( i x ) FEATURE:
        ( A ) LOCATION:306
        ( B ) NAME/KEY:N:G or A (ix) FEATURE:
    (A) LOCATION:366
    (B) NAME/KEY:N:C or T (ix) FEATURE:
    (A) LOCATION:370
    (B) NAME/KEY:N:T or C (ix) FEATURE:
    (A) LOCATION:375
    (B) NAME/KEY:N:A or T (ix) FEATURE:
    (A) LOCATION:471
    (B) NAME/KEY:N:T or C (ix) FEATURE:
    (A) LOCATION:489
    (B) NAME/KEY:N:T or G (xi) SEQUENCE DESCRIPTION:SEQ ID NO:2:

```
GCT CCC GAA CGT ATN GAC TGG CGG GCT AAG                 30
GGC GCT GTG ACA NCG GTN GAA AAT CAA GGC                 60
NNG TGN GGT TCG TGT TGG GCG TTC TCG ACT                 90
GCC GGA AAC GTT GAA GGT CAA TGG TTC ATC                120
AAN ACC GGT CAG CTT GTC AGT CTG AGC AAA                150
CAG CAA TTG GTC GAC TGT GAC ANG GNG GCC                180
NAG GGA TGC AAT GGT GGA TGG CCA NCC AGT                210
TCN TAC CTG GAA ATC ATG NAT ATG GGN GGT                240
TTG GAG TCC GAA AGC GAC TAT CCC TAT GTT                270
GGT GTG GAA CAA ACG TGT GCC CTG AAC AAG                300
GAG AAN CTG GTA GCC AAA ATC GAT GAT TCG                330
ATT GTT CTG GGT CCG GAG GAG GAG GAC CAC                360
GCC GCN TAT NTG GCN GAA CAC GGA CCG TTG                390
AGT ACG CTG CTC AAT GCC GTC GCT CTT CAG                420
TAC TAC CAG TCC GGA GTA CTC AAA CCG ACC                450
TTT GAG GAG TGT CCG GAT ACN GAG TTG AAC                480
CAC GCG GTN CTC ACC GTC GGC TAT GAC AAG                510
GAA GGC GAT ATG CCA TAC TGG ATC ATC AAG                540
AAT AGT TGG GGT ACC GAC TGG GGC GAG AAA                570
GGC TAC TTC CGA CTC TTC CGA GGA GAT TGC                600
ACG TGT GGA ATC AAC CGC ATG GCA ACA TCC                630
GCG ATC ATC AAG AAA TGA                                648
```

(2) INFORMATION FOR SEQ ID NO:3:

(i) SEQUENCE CHARACTERISTICS:
    (A) LENGTH: 648
    (B) TYPE:nucleic acid
    (C) STRANDEDNESS:single
    (D) TOPOLOGY: linear (ii) MOLECULE TYPE:cDNA to mRNA (vi) ORIGINAL SOURCE:
    (A) ORGANISM:Paragonimus westermani metacecaria ( B ) CELL TYPE:

( C ) CELL LINE:

( i x ) FEATURE:

( x i ) SEQUENCE DESCRIPTION:SEQ ID NO:3:

| | | | | | | | | | | |
|---|---|---|---|---|---|---|---|---|---|---|
| GCT | CCC | GAA | CGT | ATT | GAC | TGG | CGG | GCT | AAG | 30 |
| Ala | Pro | Glu | Arg | Ile | Asp | Trp | Arg | Ala | Lys | |
| | | | | 5 | | | | | 10 | |
| GGC | GCT | GTG | ACA | GCG | GTT | GAA | AAT | CAA | GGC | 60 |
| Gly | Ala | Val | Thr | Ala | Val | Glu | Asn | Gln | Gly | |
| | | | | 15 | | | | | 20 | |
| TCG | TGC | GGT | TCG | TGT | TGG | GCG | TTC | TCG | ACT | 90 |
| Ser | Cys | Gly | Ser | Cys | Trp | Ala | Phe | Ser | Thr | |
| | | | | 25 | | | | | 30 | |
| GCC | GGA | AAC | GTT | GAA | GGT | CAA | TGG | TTC | ATC | 120 |
| Ala | Gly | Asn | Val | Glu | Gly | Gln | Trp | Phe | Ile | |
| | | | | 35 | | | | | 40 | |
| AAA | ACC | GGT | CAG | CTT | GTC | AGT | CTG | AGC | AAA | 150 |
| Lys | Thr | Gly | Gln | Leu | Val | Ser | Leu | Ser | Lys | |
| | | | | 45 | | | | | 50 | |
| CAG | CAA | TTG | GTC | GAC | TGT | GAC | AGG | GTG | GCC | 180 |
| Gln | Gln | Leu | Val | Asp | Cys | Asp | Arg | Val | Ala | |
| | | | | 55 | | | | | 60 | |
| CAG | GGA | TGC | AAT | GGT | GGA | TGG | CCA | GCC | AGT | 210 |
| Gln | Gly | Cys | Asn | Gly | Gly | Trp | Pro | Ala | Ser | |
| | | | | 65 | | | | | 70 | |
| TCC | TAC | CTG | GAA | ATC | ATG | TAT | ATG | GGC | GGT | 240 |
| Ser | Tyr | Leu | Glu | Ile | Met | Tyr | Met | Gly | Gly | |
| | | | | 75 | | | | | 80 | |
| TTG | GAG | TCC | GAA | AGC | GAC | TAT | CCC | TAT | GTT | 270 |
| Leu | Glu | Ser | Glu | Ser | Asp | Tyr | Pro | Tyr | Val | |
| | | | | 85 | | | | | 90 | |
| GGT | GTG | GAA | CAA | ACG | TGT | GCC | CTG | AAC | AAG | 300 |
| Gly | Val | Glu | Gln | Thr | Cys | Ala | Leu | Asn | Lys | |
| | | | | 95 | | | | | 100 | |
| GAG | AAG | CTG | GTA | GCC | AAA | ATC | GAT | GAT | TCG | 330 |
| Glu | Lys | Leu | Val | Ala | Lys | Ile | Asp | Asp | Ser | |
| | | | | 105 | | | | | 110 | |
| ATT | GTT | CTG | GGT | CCG | GAG | GAG | GAG | GAC | CAC | 360 |
| Ile | Val | Leu | Gly | Pro | Glu | Glu | Glu | Asp | His | |
| | | | | 115 | | | | | 120 | |
| GCC | GCC | TAT | TTG | GCA | GAA | CAC | GGA | CCG | TTG | 390 |
| Ala | Ala | Tyr | Leu | Ala | Glu | His | Gly | Pro | Leu | |
| | | | | 125 | | | | | 130 | |
| AGT | ACG | CTG | CTC | AAT | GCC | GTC | GCT | CTT | CAG | 420 |
| Ser | Thr | Leu | Leu | Asn | Ala | Val | Ala | Leu | Gln | |
| | | | | 135 | | | | | 140 | |
| TAC | TAC | CAG | TCC | GGA | GTA | CTC | AAA | CCG | ACC | 450 |
| Tyr | Tyr | Gln | Ser | Gly | Val | Leu | Lys | Pro | Thr | |
| | | | | 145 | | | | | 150 | |
| TTT | GAG | GAG | TGT | CCG | GAT | ACT | GAG | TTG | AAC | 480 |
| Phe | Glu | Glu | Cys | Pro | Asp | Thr | Glu | Leu | Asn | |
| | | | | 155 | | | | | 160 | |
| CAC | GCG | GTT | CTC | ACC | GTC | GGC | TAT | GAC | AAG | 510 |
| His | Ala | Val | Leu | Thr | Val | Gly | Tyr | Asp | Lys | |
| | | | | 165 | | | | | 170 | |
| GAA | GGC | GAT | ATG | CCA | TAC | TGG | ATC | ATC | AAG | 540 |
| Glu | Gly | Asp | Met | Pro | Tyr | Trp | Ile | Ile | Lys | |
| | | | | 175 | | | | | 180 | |
| AAT | AGT | TGG | GGT | ACC | GAC | TGG | GGC | GAG | AAA | 570 |

| | | | | | | | | | | |
|---|---|---|---|---|---|---|---|---|---|---|
| | Asn | Ser | Trp | Gly | Thr | Asp | Trp | Gly | Glu | Lys |
| | | | | | 185 | | | | | 190 |
| GGC | TAC | TTC | CGA | CTC | TTC | CGA | GGA | GAT | TGC | 600 |
| Gly | Tyr | Phe | Arg | Leu | Phe | Arg | Gly | Asp | Cys | |
| | | | | 195 | | | | | 200 | |
| ACG | TGT | GGA | ATC | AAC | CGC | ATG | GCA | ACA | TCC | 630 |
| Thr | Cys | Gly | Ile | Asn | Arg | Met | Ala | Thr | Ser | |
| | | | | 205 | | | | | 210 | |
| GCG | ATC | ATC | AAG | AAA | TGA | | | | | 648 |
| Ala | Ile | Ile | Lys | Lys | *** | | | | | |
| | | | | 215 | | | | | | |

( 2 ) INFORMATION FOR SEQ ID NO:4:

( i ) SEQUENCE CHARACTERISTICS:
        ( A ) LENGTH: 648
        ( B ) TYPE:nucleic acid
        ( C ) STRANDEDNESS:single
        ( D ) TOPOLOGY:linear ( i i ) MOLECULE TYPE:cDNA to mRNA ( v i ) ORIGINAL SOURCE:
        ( A ) ORGANISM:Paragonimus westermani metacecaria
        ( B ) CELL TYPE:
        ( C ) CELL LINE:

( i x ) FEATURE:

( x i ) SEQUENCE DESCRIPTION:SEQ ID NO:4:

| | | | | | | | | | | |
|---|---|---|---|---|---|---|---|---|---|---|
| GCT | CCC | GAA | CGT | ATG | GAC | TGG | CGG | GCT | AAG | 30 |
| Ala | Pro | Glu | Arg | Met | Asp | Trp | Arg | Ala | Lys | |
| | | | | 5 | | | | | 10 | |
| GGC | GCT | GTG | ACA | CCG | GTG | GAA | AAT | CAA | GGC | 60 |
| Gly | Ala | Val | Thr | Pro | Val | Glu | Asn | Gln | Gly | |
| | | | | 15 | | | | | 20 | |
| GAG | TGT | GGT | TCG | TGT | TGG | GCG | TTC | TCG | ACT | 90 |
| Glu | Cys | Gly | Ser | Cys | Trp | Ala | Phe | Ser | Thr | |
| | | | | 25 | | | | | 30 | |
| GCC | GGA | AAC | GTT | GAA | GGT | CAA | TGG | TTC | ATC | 120 |
| Ala | Gly | Asn | Val | Glu | Gly | Gln | Trp | Phe | Ile | |
| | | | | 35 | | | | | 40 | |
| AAG | ACC | GGT | CAG | CTT | GTC | AGT | CTG | AGC | AAA | 150 |
| Lys | Thr | Gly | Gln | Leu | Val | Ser | Leu | Ser | Lys | |
| | | | | 45 | | | | | 50 | |
| CAG | CAA | TTG | GTC | GAC | TGT | GAC | ATG | GCG | GCC | 180 |
| Gln | Gln | Leu | Val | Asp | Cys | Asp | Met | Ala | Ala | |
| | | | | 55 | | | | | 60 | |
| GAG | GGA | TGC | AAT | GGT | GGA | TGG | CCA | TCC | AGT | 210 |
| Glu | Gly | Cys | Asn | Gly | Gly | Trp | Pro | Ser | Ser | |
| | | | | 65 | | | | | 70 | |
| TCA | TAC | CTG | GAA | ATC | ATG | GAT | ATG | GGT | GGT | 240 |
| Ser | Tyr | Leu | Glu | Ile | Met | Asp | Met | Gly | Gly | |
| | | | | 75 | | | | | 80 | |
| TTG | GAG | TCC | GAA | AGC | GAC | TAT | CCC | TAT | GTT | 270 |
| Leu | Glu | Ser | Glu | Ser | Asp | Tyr | Pro | Tyr | Val | |
| | | | | 85 | | | | | 90 | |
| GGT | GTG | GAA | CAA | ACG | TGT | GCC | CTG | AAC | AAG | 300 |
| Gly | Val | Glu | Gln | Thr | Cys | Ala | Leu | Asn | Lys | |
| | | | | 95 | | | | | 100 | |
| GAG | AAA | CTG | GTA | GCC | AAA | ATC | GAT | GAT | TCG | 330 |
| Glu | Lys | Leu | Val | Ala | Lys | Ile | Asp | Asp | Ser | |
| | | | | 105 | | | | | 110 | |
| ATT | GTT | CTG | GGT | CCG | GAG | GAG | GAG | GAC | CAC | 360 |

-continued

| | | | | | | | | | | |
|---|---|---|---|---|---|---|---|---|---|---|
| Ile | Val | Leu | Gly | Pro 115 | Glu | Glu | Glu | Asp | His 120 | |
| GCC Ala | GCT Ala | TAT Tyr | CTG Leu | GCT Ala 125 | GAA Glu | CAC His | GGA Gly | CCG Pro | TTG Leu 130 | 390 |
| AGT Ser | ACG Thr | CTG Leu | CTC Leu | AAT Asn 135 | GCC Ala | GTC Val | GCT Ala | CTT Leu | CAG Gln 140 | 420 |
| TAC Tyr | TAC Tyr | CAG Gln | TCC Ser | GGA Gly 145 | GTA Val | CTC Leu | AAA Lys | CCG Pro | ACC Thr 150 | 450 |
| TTT Phe | GAG Glu | GAG Glu | TGT Cys | CCG Pro 155 | GAT Asp | ACC Thr | GAG Glu | TTG Leu | AAC Asn 160 | 480 |
| CAC His | GCG Ala | GTG Val | CTC Leu | ACC Thr 165 | GTC Val | GGC Gly | TAT Tyr | GAC Asp | AAG Lys 170 | 510 |
| GAA Glu | GGC Gly | GAT Asp | ATG Met | CCA Pro 175 | TAC Tyr | TGG Trp | ATC Ile | ATC Ile | AAG Lys 180 | 540 |
| AAT Asn | AGT Ser | TGG Trp | GGT Gly | ACC Thr 185 | GAC Asp | TGG Trp | GGC Gly | GAG Glu | AAA Lys 190 | 570 |
| GGC Gly | TAC Tyr | TTC Phe | CGA Arg | CTC Leu 195 | TTC Phe | CGA Arg | GGA Gly | GAT Asp | TGC Cys 200 | 600 |
| ACG Thr | TGT Cys | GGA Gly | ATC Ile | AAC Asn 205 | CGC Arg | ATG Met | GCA Ala | ACA Thr | TCC Ser 210 | 630 |
| GCG Ala | ATC Ile | ATC Ile | AAG Lys | AAA Lys 215 | TGA *** | | | | | 648 |

( 2 ) INFORMATION FOR SEQ ID NO:5:

( i ) SEQUENCE CHARACTERISTICS:
        ( A ) LENGTH: 25
        ( B ) TYPE:amino acid
        ( C ) STRANDEDNESS:
        ( D ) TOPOLOGY:linear ( i i ) MOLECULE TYPE:peptide ( v i ) ORIGINAL SOURCE:
        ( A ) ORGANISM:Paragonimus westermani metacecaria
        ( B ) CELL TYPE:
        ( C ) CELL LINE:

( i x ) FEATURE:
        ( A ) OTHER INFORMATION:
            The 22nd and 25th residues, Xaa, are to be cysteine
            which could not be detected with this PTH analyser
            system. The amino acid sequence shown below is
            N-terminal 25 amino acids of the purified native
            cysteine protease.

( x i ) SEQUENCE DESCRIPTION:SEQ ID NO:5:

| | | | | | | | | | |
|---|---|---|---|---|---|---|---|---|---|
| Ala | Pro | Glu | Ser | Ile 5 | Asp | Trp | Arg | Glu | Lys 10 |
| Gly | Ala | Val | Ala | Pro 15 | Val | Glu | Asp | Gln | Gly 20 |
| Ser | Xaa | Gly | Ser | Xaa 25 | | | | | |